United States Patent [19]

Strobridge

[11] Patent Number: 4,917,882

[45] Date of Patent: Apr. 17, 1990

[54] GEL-TYPE SUNSCREEN COMPOSITION

[75] Inventor: John R. Strobridge, Comstock Park, Mich.

[73] Assignee: Amway Corporation, Ada, Mich.

[21] Appl. No.: 324,564

[22] Filed: Mar. 16, 1989

[51] Int. Cl.$^4$ .......................... A61K 7/42; A61K 7/44
[52] U.S. Cl. .......................................... 424/59; 424/60
[58] Field of Search .................................... 424/59, 60

[56] References Cited

U.S. PATENT DOCUMENTS

| | | | |
|---|---|---|---|
| 4,193,989 | 3/1980 | Teng et al. | 424/59 |
| 4,486,405 | 12/1984 | Klein | 424/59 |
| 4,559,225 | 12/1985 | Fourman | 424/59 |
| 4,671,955 | 6/1987 | Palinczar | 424/59 |
| 4,683,134 | 7/1987 | Palinczar | 424/59 |
| 4,686,099 | 8/1987 | Palinczar | 424/59 |
| 4,710,371 | 12/1987 | Palinczar | 424/59 |
| 4,731,242 | 3/1988 | Palinczar | 424/59 |
| 4,749,563 | 6/1988 | Georgalas | 424/59 |
| 4,781,914 | 11/1988 | Deckner | 424/59 |
| 4,810,489 | 3/1989 | Murray et al. | 424/59 |
| 4,810,490 | 3/1989 | Dixon | 424/59 |

FOREIGN PATENT DOCUMENTS

| | | |
|---|---|---|
| 2408663 | 8/1975 | Fed. Rep. of Germany . |
| 2833711 | 2/1979 | Fed. Rep. of Germany . |

OTHER PUBLICATIONS

Leroy et al, C.A. 105:11839t (1986).

*Primary Examiner*—Shep K. Rose
*Attorney, Agent, or Firm*—Willian Brinks Olds Hofer Gilson & Lione

[57] ABSTRACT

A gel-type sunscreen composition is disclosed. The composition includes between about 1 and about 30 percent of a sunscreen agent, between about 5 and about 20 percent polyethylene, and between about 20 and about 94 percent of an benzoate ester. A method of forming this composition is also disclosed.

28 Claims, No Drawings

GEL-TYPE SUNSCREEN COMPOSITION

BACKGROUND OF THE INVENTION

The present invention relates to the field of sunscreen compositions, i.e. compositions which, when applied to the skin, provide protection against the damaging effects of ultraviolet radiation. More particularly, the invention relates to the field of sunscreen compositions which are in the form of a gel, preferably anhydrous.

In recent years, the general public has become more and more aware of the damaging effects of ultraviolet radiation from the sun. Consequently, sunscreen compositions have become popular for people who spend time in the sun. Generally, such sunscreen compositions include active sunscreen agents, such as Padimate O, which absorb ultraviolet light in the erythemal region (280–320 nanometers), i.e. the region linked to erythema and skin cancer. Those compositions formulated for greater protection typically also include a sunscreen agent, such as oxybenzone, which absorbs ultraviolet light in a broader range (e.g. 280–340).

A challenge in formulating a sunscreen composition is to produce a composition with good substantivity, i.e. retention on the skin. Naturally, the effectiveness of a sunscreen composition is tied directly to its ability to stay in place on the skin of the user for the entire time the user is in the sun. As a result, it is important that the composition be resistant to being rubbed off or washed off in water.

To make a sunscreen resistant to being washed off in water, i.e. waterproof, is particularly important in view of the fact that many consumers use sunscreen compositions in connection with water sports. Also, because sunscreen compositions are often used on hot days and/or in connection with strenuous physical activities, it is important that the compositions be waterproof so that it is not lost due to perspiration.

U.S. Pat. No. 4,663,157 to Brock describes an oil in water emulsion sunscreen composition which is reportedly resistant to rubbing off. The composition includes between about 1 and about 20 percent of a sunscreen agent, between about 0.25 and about 3 percent of a copolymer of ethylene and acrylic acid, between about 2 and about 10 percent emulsifier and between about 70 and about 96 percent water. The ratio of the sunscreen agent to the copolymer is stated to be between about 1:12 and about 15:1. This copolymer in this ratio is stated to improve the substantivity, particularly the resistance to rubbing off, of the composition.

U.S. Pat. No. 4,699,779 to Palinczar describes a sunscreen which is reported to be waterproof. The composition includes from about 15 to about 95 percent water, from about 1 to about 30 percent of an active sunscreen agent, from about 0.1 to about 6 percent ethylcellulose, from about 0.01 to about 12 percent surface active agent, and from about 0.03 to about 5 percent alkaline dispersion promoting agent.

U.S. Pat. No. 4,731,242 to Palinczar describes a sunscreen composition which is also reported to be waterproof. The disclosed composition includes from 15 to about 90 percent monohydric alcohols, from about 1 to about 30 percent of an active sunscreen agent, from about 0.1 to about 40 percent polyamide polymer, from about 0.1 to about 5 percent acrylic acid crosslinked polymer, and from about 0.1 to about 8 percent alkaline neutralizing agent.

SUMMARY OF THE INVENTION

Briefly stated, the present invention is a gel-type sunscreen composition. The composition includes between about 1 and about 30 percent of a sunscreen agent. In addition, the sunscreen composition includes between about 5 and about 20 percent polyethylene and between about 20 and about 94 percent of a benzoate ester.

In accordance with a preferred embodiment, the gel-type composition is anhydrous and contains about 78 percent of an ester of benzoic acid with alcohols having from 12 to 15 carbons. This preferred composition further includes about 14 percent polyethylene, about 4 percent Padimate O, and about 3 percent water insoluble emollients. The preferred composition further includes a suitable amount of dyes to impart a bronze color.

In accordance with the method aspect of the present invention, between about 1 and about 30 percent of a sunscreen agent, between about 5 and about 25 percent polyethylene to between about 20 and about 95 percent of a benozic ester are combined. This mixture is agitated and heated to a temperature and for a time sufficient to dissolve the polyethylene in the benzoate ester. After the polyethylene is dissolved in the benozate ester, the mixture is cooled while agitating to thereby produce a gelled sunscreen composition.

In accordance with a less preferred embodiment, the gel-type composition of the present invention can itself be put into an oil in water emulsion. In such an embodiment, an emulsifier and high shear blending would be used to put droplets of the gel-type composition into a water emulsion.

The present invention has been found to be advantageous in that the compositions made have been found to possess remarkable substantivity, even when immersed in water for 80 minutes or more. As will be discussed below in connection with the examples, some tests have indicated that the efficacy of the composition can actually increase after immersion in water. Accordingly, the preferred compositions of the present invention can be designated as "waterproof" or "water resistant" under the guidelines published in the FDA monograph published in the *Federal Register*. Vol. 43, No. 166, pp. 38206–38269.

The present invention also provides the advantage that, unlike most anhydrous gel-type compositions, the composition has a generally non-greasy feel to it.

The present invention is also advantageous in that it can be made with an aesthetically pleasing appearance. In particular, the preferred composition has a pleasing appearance because the benzoate ester and polyethylene provide a generally translucent medium. Consequently, the composition can include dyes and the like to impart desirable colors, e.g. a bronzing color, to the composition.

The invention provides the further advantage that the consistency, e.g. the viscosity and homogeneity, of the composition is stable over a relatively wide range of temperatures. In contrast, most gel-type products made with paraffin and the like have a tendency to liquify and/or separate at elevated temperatures, e.g. on a hot beach. Also, some products, such as oil in water emulsion products, have a tendency to freeze at cold temperatures, e.g. on a ski slope. However, the preferred composition of the present invention is generally stable at temperatures below 0° and above 135° F.

It is noted that, unless otherwise indicated, the percentages stated in this specification and the appended claims are intended to refer to percentages by weight of the total sunscreen composition.

The present invention, together with attendant objects and advantages, will be best understood with reference to the detailed description below.

DETAILED DESCRIPTION OF THE PREFERRED EMBODIMENTS

The sunscreen product of the present invention is a gel-type composition, preferably anhydrous. This format has been found to be advantageous for particular applications. In particular, some consumers prefer an oil type sunscreen product, expecting the oil type product to soften the skin and enhance the tanned appearance of the skin. A gel-type composition provides this oil appearance in a format which is viscous enough to be easier to handle by the consumer. In other words, the gel-type composition does not run off the surfaces it is applied to.

The gel-type composition is also advantageous because it can be made to be clear or translucent. In contrast, oil in water and water in oil emulsion are typically opaque. The clear or translucent gel-type composition is desirable because it can be used with dyes and the like to impart a selected color to the composition. Most preferably, dyes can be used to create a bronze color in the composition which is perceived to enhance the tanned appearance of the user.

The gel-type composition also has the advantage that it can be used to suspend solids more readily than a more liquid composition. Although not preferred in the present invention, solids such as titanium oxide can be suspended in the gel-type composition to thereby opacify the composition and add to the UV absorption of the composition.

Anhydrous gel-type compositions are also preferred over water containing emulsions for cold weather applications. As mentioned above, compositions containing water can freeze at low temperatures, thus rendering the composition unusable.

The composition of the present invention includes a benzoate ester in an amount between about 20 and about 95 percent of the composition. Preferably, the benzoate ester is included at between about 50 and about 80 percent.

The benzoate ester is important to the composition of the present invention because it provides a translucent, non-oily feeling, anhydrous vehicle which is well suited for carrying the sunscreen agents. In particular, benzoate esters do not interfere with the UV absorption of typical sunscreen agents. In contrast, compounds such as mineral oil have been found to shift the absorbance curve of agents such as Padimate O, thereby reducing their ability to absorb UV radiation in the erythemal region.

The preferred benzoate ester to use is an ester of benzoic acid with alcohols having from 12 to 15 carbons. Most preferably, the benzoate ester is one such as that sold by FINTEX under the designation "Finsolve Tn." Alternatively, benzoate esters such as "Finsolve P" and "Finsolve SB", both from FINTEX, can be used.

The sunscreen composition of the present invention also includes between about 5 and about 25 percent polyethylene, preferably between about 10 and about 15 percent.

The polyethylene is important to the present composition because it acts as the gelling agent for the composition. In particular, the polyethylene produces a gel because of its tendency to form a crystalline latice structure within the benzoate ester as it cools from temperatures typically in excess of about 93° C. The exact properties of the crystalline structure, i.e. the size and extent of the crystallinity, can be controlled by the cooling rate and type of agitation of the mix during cooling. These properties of the crystalline structure affect the rheology and viscosity of the final product.

Preferably, the polyethylene used in the composition will have a molecular weight of between about 1,500 and about 100,000. More preferably, the molecular weight will be about 3,800. Preferably, the polyethylene will have a hardness of between about 0.5 to about 90.0 (dmm by ASTMD-5) and a drop point temperature between about 92° and about 117° C. (ASTMD-3954). Most preferably, the polyethylene is one such as that obtained from Allied Signal under the designation "polyethylene 617A". This particular polyethylene has a hardness of 7.0 and a drop point temperature of 102° C. Other suitable polyethylenes from Allied Signal are polyethylenes designated 6, 6A, 7, 7A, 8, 8A, 9, 9A, and 617. Suitable polyethylenes can also be obtained from Eastman Chemical under the trade name "Epolene," and from U.S. Industrial Chemicals under the trade name "Microthene" with the numbers ML-733, MN-714, or MN-722.

The composition of the present invention includes between about 1 and about 30 percent of an active sunscreen agent. As used herein, the term active sunscreen agent is intended to refer to a compound which absorbs ultraviolet radiation in the range which is harmful to human skin. Naturally, it is important that the sunscreen agent is non-irritating, non-toxic and compatible with the other ingredients used in the composition.

Suitable active sunscreen agents include the following compounds: Padimate O (octyl p-dimethylaminobenzoate); Padimate A (amyl p-dimethylaminobenzoate); Oxybenzone (2-hydroxy-4-methoxybenzophenone); ethylhexyl p-methoxycinnamate; PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4-[bis(hydroxypropyl)]-aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); 2-phenylbenzimidazole-5-sulfonic acid); Sulisobenzone (5-benzoyl-4-hydroxy-2-methoxybenzenesulfonic acid); triethanolamine salicylate; 4-tert.butyl-4-methoxydibenzoylmethane; and benzalphthalide. Preferably, a combination of sunscreen agents selected from the group consisting of Padimate O, Oxybenzone, ethylhexyl p-methoxycinnamate, and octyl salicylate is used.

As mentioned, the present invention may contain from about 1% to about 30% by weight of one or a combination of these active sunscreen agents. The preferred total amount of the active sunscreen agent is dependent upon the particular agents chosen as well as the particular SPF value (sun protection factor) desired to be obtained. The preferred sunscreen agents in the present invention are Padimate O in amounts from 0.5% to about 8% by weight; oxybenzone in amounts from 0.5% to about 6% by weight, and ethylhexyl p-methoxycinnamate in amounts from about 0.5% by weight to about 7% by weight.

The preferred composition of the present invention also includes from about 1 to about 30 percent of water insoluble emollients, i.e. compounds which are known to act as skin softeners. Preferably, the water insoluble emollients are selected from the group consisting of lanolin, isopropyl myristate, glyceryl stearate, cetyl alcohol, and dimethicone, together with combinations thereof.

The preferred composition may also include a fragrance in order to impart an appropriate pleasing odor to the composition.

The preferred composition may further include an appropriate amount of a preservative selected so as to provide protection against spoilage. Because the preferred composition is anhydrous, the risk of microorganism growth within the composition is quite small. As such, the most preferred embodiment contains only about 0.05 percent of a preservative such as propyl parabin. This preservative is used only to guard against the risk that some water has accidentally come into the composition.

Although the preferred composition is translucent, alternative embodiments may include between about 0.5 and about 25 percent of suspended particulate matter. Preferably, this suspended particulate matter will be an opacifyer, such as titanium dioxide, which not only adds a white pigment to the composition, but also acts as a sunscreen agent in and of itself. In addition to titanium oxide, other compounds that can be used for this purpose include zinc oxide, talc, kaolin, calcium carbonate, and magnesium oxide, as well as combinations thereof.

In general, the preferred method of producing the gel-type sunscreen composition of the present invention begins by combining the active sunscreen agent, the benzoate ester, and the polyethylene. This mixture is heated and agitated to a temperature and for a time sufficient to dissolve the polyethylene in the benzoate ester. Preferably, the temperature to which the mixture is heated will be above about 93° C. After the polyethylene is all dissolved, the mixture is cooled while continuing the agitation to thereby form the gelled composition will the sunscreen agent well distributed therein. Preferably, the temperature to which the composition is cooled while agitating is below about 57° C.

More preferably, the mixture is heated to a temperature between about 93° and about 104° C. to dissolve the polyethylene. More preferably, the agitation is continued until the mixture has cooled to about 49° C. Also, the mixture is preferably agitated during the cooling stage by passing it through an in-line mill or homogenizer.

In the most preferred embodiment, a pre-blend, containing 78 percent Finsolve Tn, 14 percent polyethylene 617A, and 4.0 percent Padimate O, is mixed in a sweep wall type mixer. The pre-blend is heated to a temperature between about 93° and about 104° C. Although varying with the batch size, the polyethylene will typically be dissolved after about 20 minutes at this temperature with agitation. After the polyethylene is completely dissolved, the mixture is cooled to a temperature between about 82° and about 93° C. The following ingredients are then added while maintaining the temperature and agitation: 3.0 percent Isopropyl Myristate, 0.1 percent lanolin, 0.05 percent preservative, 0.00075 Yellow No. 11, 0.00075 Red No. 17, 0.00005 Green No. 6. After these ingredients are well dispersed, the mixture is cooled further and is also passed through an in-line mill, such as a Gifford Wood mill, to provide additional agitation, i.e. in addition to the agitation provided by the sweep wall mixer which is kept running throughout the procedure. When the temperature of the mixture reaches about 60° to 68° C., the milling is discontinued, while the mixing is continued as the mixture is cooled to a temperature between about 49° to about 57° C. At this point, a fragrance is added, and the mixture is continued to be mixed until reaching a temperature of about 49. Although varying with the batch size, the sequential cooling from the time the polyethylene is dissolved until the mixing is stopped is typically about 1.5 hours. At this point, the mixing is discontinued and the mixture can stored or packaged immediately. Most preferably, the composition is packaged in plastic tubes.

As mentioned above, the gel-type composition of the present invention can be used to formulate a sunscreen in an oil in water emulsion format. In this less preferred embodiment, the gel-type composition containing the sunscreen agent is made first by the above-described methods. The composition is then be put into an emulsion by methods well known in the art. Typically, high shear agitation is used together with an emulsifier, preferably between about 1 and about 10 percent. A suitable emulsifier is a saponified long chain fatty acid, such as isostearic acid. Preferably, the fatty acid is saponified in situ, i.e. after the oil phase is dispersed in the water phase. Alkaline compounds such as sodium hydroxide, or ammonium hydroxide are typically used to saponify the long chain fatty acids. The resultant emulsion is characterized as having small drops of the gel-type composition which are surrounded by the external water phase. Preferably, the emulsion will contain between about 45 and about 90 percent water. Such emulsions are typically opaque.

EXAMPLES

Examples 1–5 were made with the following formalae. Example 1 was conducted in accordance with the most preferred embodiment of the present invention. Example 2 was conducted as a comparative example in that it did not include polyethylene.

| Ingredient | Weight Percent | | | | |
| --- | --- | --- | --- | --- | --- |
| | Ex. 1 | Ex. 2 | Ex. 3 | Ex. 4 | Ex. 5 |
| C12–15 Alcohols Benzoate | 78.35 | 92.35 | 74.35 | 64.35 | 62.35 |
| Padimate 0 | 4.0 | 4.0 | 4.0 | 8.0 | 8.0 |
| Polyethylene | 14.0 | — | 18.0 | 14.0 | 14.0 |
| Isopropyl Myristate | 3.00 | 3.0 | 3.0 | — | — |
| Lanolin | 0.1 | 0.1 | 0.1 | 0.1 | 0.1 |
| Fragrance | 0.5 | 0.5 | 0.5 | 0.5 | 0.5 |
| Preservative | 0.05 | 0.05 | 0.05 | 0.05 | 0.05 |
| Yellow No. 11 | 0.00075 | — | — | 0.00075 | — |
| Red No. 17 | 0.00075 | — | — | 0.00075 | — |
| Green No. 6 | 0.00005 | — | — | 0.00005 | — |
| Oxybenzone | — | — | — | 6.0 | 6.0 |
| Titanium Dioxide | — | — | — | — | 2.0 |
| Ethylhexyl p-Methoxycinnamate | — | — | — | 7.0 | 7.0 |

These ingredients were put together as described above in connection with the most preferred embodiment, i.e. with the same order of addition, temperatures, and equipment.

It was observed that Example 1 resulted in an aesthetically pleasing translucent bronze colored gel-type composition. The composition was judged to have a non-greasy feel. In tests described below, the substantivity of the composition, particularly in water, was found to be remarkable.

Example 2 was performed the same as Example 1 except that it contained no polyethylene. This composition had a low viscosity which made it unappealing for a sunscreen composition. The composition also showed low substantivity.

Example 3 was performed the same as Example 1 with the exception that the amount of polyethylene was increased to 18.0 percent. Also, no dyes were included in this formulation. The resultant composition was clear to translucent and showed excellent substantivity.

Example 4 was performed the same as Example 1 with the exceptions that more sunscreen agents were included and isopropyl myristate was excluded. The additional sunscreen agents were oxybenzone and ethylhexyl p-methoxycinnamate. This composition had an appearance similar to that of Example 1. The composition was slightly more viscous that that of Example 1 because of the increased solids contributed by the oxybenzone. The substantivity results were excellent.

Example 5 was performed the same as Example 4 except that 2.0 percent titanium oxide was added to the composition, and no dyes were added. This yielded a white opaque gel which had a viscosity similar to Example 4 and excellent substantativity.

The sunscreen compositions made in the examples above were tested to compare their substantivity to a surface upon exposure to water. The test was designed to be simple and reproducible and yet provide an evaluation of the substantivity of the compositions in a worst case situation.

The test began by spreading a thin layer, i.e. 0.002 ml/cm$^2$, of the composition on a glass slide. The composition was allowed to dry down for 20 minutes at ambient temperatures. The glass slide was then placed in a 250 ml. beaker containing soft water, i.e. 5 grains. Earlier tests had shown that substantivity was harder to achieve in distilled water than in either soft water, hard water (12+ grains) or sea water. Soft water was thus chosen to best reflect the real world. The water in the beaker was stirred by magnetic stirring bar at a medium speed. At various times, the water and slide were viewed to determine if the composition had come off of the slide. In particular, if the water turned milky with solubilized/dispersed composition, or if flakes or other pieces of the composition were floating in the water, then that composition was given a poor substantivity rating.

Examples 1 and 3–5 all showed good substantivity in this test for at least 80 minutes in the stirred water. In particular, the composition stayed in place on the glass slide. Further tests confirmed that, if a composition had remained in place on the glass slide in stirred water for 80 minutes, the composition would likewise remain in place for several hours under the same condition.

In addition to the aforementioned in vitro test, studies were also conducted to evaluate the performance of sunscreen compositions made according to the preferred embodiments as applied to human skin which was subjected to UV radiation, with and without being immersed in water. In particular, the study was conducted by an independent laboratory in conformance with the monograph published in the *Federal Register*. Vol. 43, No. 166, pp. 38206–38269. Basically, the test monitored the Sun Protection Factor (SPF) of each of the compositions before and after immersion in water.

This in vivo testing confirmed that the substantivity shown in the in vitro test described above was indeed representative of the substantivity obtained in the real world. In addition, a surprising result was observed that the SPF of the most preferred composition actually increased after 80 minutes of exposure to water. In particular, the SPF before immersion was measured at 6.1 while the SPF after immersion was measured at 6.7. This result was particularly surprising because most sunscreen compositions generally lose effectiveness after immersion in water.

It should be noted that, although much of the discussion has involved the use of the composition as a gel-type sunscreen composition for direct application to the skin, the gel-type composition can also be put into an oil in water emulsion. Certainly, this and all other modifications which are within the ordinary skill in the art to make are considered to lie within the scope of the invention as defined by the appended claims.

I claim:

1. A method of producing a gel-type sunscreen composition comprising the steps of:
   combining between about 1 and about 30 percent of sunscreen agent, between about 5 and about 25 percent polyethylene to between about 20 and about 95 percent of a benzoic ester;
   agitating and heating the mixture to a temperature and for a time sufficient to dissolve the polyethylene in the benzoate ester;
   after the polyethylene is dissolved in the benzoate ester, cooling the mixture while agitating to thereby produce a gelled sunscreen composition.

2. The method of claim 1 wherein the polyethylene is added in an amount between about 10 and about 15 percent.

3. The method of claim 1 wherein the benzoate ester is added in an amount between about 50 and 80 percent.

4. The method of claim 3 wherein the polyethylene is added in an amount between about 10 and about 15 percent.

5. The method of claim 1 wherein the benzoate ester is an ester of benzoic acid and alcohols having 12 to 15 carbons.

6. The method of claim 5 wherein the benzoate ester is added in an amount between about 50 and 80 percent.

7. The method of claim 6 wherein the polyethylene is added in an amount between about 10 and about 15 percent.

8. The method of claim 1 wherein the sunscreen agent is selected from the group consisting of Padimate O, Padimate A, oxybenzone, ethylhexyl p-methoxycinnamate, octyl salicylate, and combinations thereof.

9. The method of claim 1 further comprising of adding up to about 5 percent of one or more oil soluble dyes.

10. The method of claim 1 further comprising of adding up to about 20 percent suspended particulate matter selected from the group consisting of titanium dioxide, zinc oxide, talc, kaolin, calcium carbonate, magnesium oxide, and combinations thereof.

11. The method of claim 1 further comprising the step of adding up to about 30 percent of water insoluble emollient selected from the group consisting of lanolin, isopopyl myristate, glyceryl stearate, cetyl alcohol, dimethicone, and combinations thereof.

12. The method of claim 1 wherein the temperature to which the mixture is heated is above about 93° C.

13. The method of claim 1 wherein the temperature to which the mixture is cooled while agitating is below about 57° C.

14. A polyethylene gel-type sunscreen composition prepared in accordance with the method of claim 1 comprising:
   between about 1 and about 30 percent of sunscreen agent;
   between about 5 and about 25 percent polyethylene; and
   between about 20 and about 94 percent of a benzoate ester.

15. The sunscreen composition of claim 14 wherein the polyethylene is present in an amount between about 10 and about 15 percent.

16. The sunscreen composition of claim 14 wherein the benzoate ester is present in an amount between about 50 and 80 percent.

17. The sunscreen composition of claim 16 wherein the polyethylene is present in an amount between about 10 and about 15 percent.

18. The sunscreen composition of claim 14 wherein the benzoate ester is an ester of benzoic acid and alcohols having 12 to 15 carbons.

19. The sunscreen composition of claim 18 wherein the benzoate ester is present in an amount between about 50 and 80 percent.

20. The sunscreen composition of claim 19 wherein the polyethylene is present in an amount between about 10 and about 15 percent.

21. The sunscreen composition of claim 14 wherein the sunscreen agent is selected from the group consisting of Padimate O, Padimate A, oxybenzone, ethylhexyl p-methoxycinnamate, octyl salicylate, and combinations thereof.

22. The sunscreen composition of claim 14 further comprising up to about 5 percent of one or more oil soluble dyes.

23. The sunscreen composition of claim 14 wherein the composition is translucent.

24. The sunscreen composition of claim 23 further comprising up to about 5 percent of one or more oil soluble dyes.

25. The sunscreen composition of claim 14 further comprising between about 0.5 and about 25 percent suspended particulate matter selected from the group consisting of titanium dioxide, zinc oxide, talc, kaolin, calcium carbonate, magnesium oxide, and combinations thereof.

26. The sunscreen composition of claim 14 further comprising from about up to about 30 percent of an oil soluble emollient selected from the group consisting of lanolin, isopopyl myristate, glyceryl stearate, cetyl alcohol, dimethicone, and combinations thereof.

27. An oil in water sunscreen composition comprising:
   the gel-type sunscreen composition of claim 14;
   between about 1 and about 10 percent of an emulsifier; and
   between about 45 and about 90 percent water.

28. A polyethylene gel-type sunscreen composition prepared in accordance with the method of claim 1 comprising:
   between about 1 and about 30 percent of sunscreen agent;
   between about 5 and about 25 percent polyethylene; and
   between about 50 and about 80 percent of an ester of benzoic acid and alcohols having from 12 to 15 carbons;
   between about 1 and about 30 percent water insoluble emollient.

* * * * *